(12) United States Patent
Shadd

(10) Patent No.: US 10,643,057 B2
(45) Date of Patent: May 5, 2020

(54) SYSTEMS AND METHODS FOR BIOMETRICALLY AUTHENTICATING A USER USING AUTHENTICATION DATA AND LIVENESS DATA

(71) Applicant: Warren M. Shadd, District Heights, MD (US)

(72) Inventor: Warren M. Shadd, District Heights, MD (US)

( * ) Notice: Subject to any disclaimer, the term of this patent is extended or adjusted under 35 U.S.C. 154(b) by 0 days.

(21) Appl. No.: 15/857,575

(22) Filed: Dec. 28, 2017

(65) Prior Publication Data

US 2018/0211094 A1 Jul. 26, 2018

Related U.S. Application Data

(60) Provisional application No. 62/439,706, filed on Dec. 28, 2016.

(51) Int. Cl.
*G06K 9/00* (2006.01)
*A61B 5/00* (2006.01)
(Continued)

(52) U.S. Cl.
CPC ........ *G06K 9/00114* (2013.01); *A61B 5/1172* (2013.01); *A61B 5/489* (2013.01);
(Continued)

(58) Field of Classification Search
CPC ......... A61B 5/02; A61B 5/1172; A61B 5/489; G06F 21/32; G06K 2009/00932;
(Continued)

(56) References Cited

U.S. PATENT DOCUMENTS

2009/0245591 A1* 10/2009 Rowe ................. G06K 9/00033
382/115
2010/0080422 A1* 4/2010 Sato .................... G06K 9/0004
382/115

(Continued)

OTHER PUBLICATIONS

U.S. International Searching Authority, International Search Report and Written Opinion, dated Mar. 12, 2018 for PCT/US17/68838 filed Dec. 28, 2017, 9 pages.

*Primary Examiner* — Ian L Lemieux
(74) *Attorney, Agent, or Firm* — Perkins Coie LLP

(57) ABSTRACT

Systems and methods for biometrically authenticating a user are disclosed. In one implementation, a biometric authentication system may include a finger scanner for capturing biometric data from a plurality of sections of a finger of a user. The finger may include a distal section, a medial section, and a proximal section. The biometric authentication system may further include one or more processors configured to cause the finger scanner to capture the biometric data from the plurality of sections of the finger of the user. The biometric data may include authentication data and liveness data. The processors may be further configured to access registered authentication data associated with the user, determine whether the captured authentication data matches the authentication biometric data, and determining, using the captured liveness data, whether the finger is a live finger. Additionally, the processors may be configured to authenticate the user after the captured authentication data is determined to match the registered authentication data and after the finger is determined to be a live finger.

15 Claims, 9 Drawing Sheets

(51) Int. Cl.
*G06F 21/32* (2013.01)
*A61B 5/1172* (2016.01)
*A61B 5/02* (2006.01)

(52) U.S. Cl.
CPC ......... *G06F 21/32* (2013.01); *G06K 9/00006* (2013.01); *G06K 9/00067* (2013.01); *G06K 9/00107* (2013.01); *G06K 9/00892* (2013.01); *A61B 5/02* (2013.01); *G06K 2009/00932* (2013.01); *G06K 2009/00939* (2013.01)

(58) Field of Classification Search
CPC ..... G06K 2009/00939; G06K 9/00006; G06K 9/00067; G06K 9/00107; G06K 9/00114; G06K 9/00892
See application file for complete search history.

(56) References Cited

U.S. PATENT DOCUMENTS

| | | | |
|---|---|---|---|
| 2011/0026783 A1* | 2/2011 | Fujii | A61B 5/117 382/124 |
| 2013/0258086 A1* | 10/2013 | Erhart | H04N 5/23219 348/77 |
| 2014/0059675 A1 | 2/2014 | Batie, Jr. et al. | |
| 2014/0241596 A1* | 8/2014 | Chen | G06K 9/00885 382/124 |
| 2015/0269452 A1* | 9/2015 | Vardy | G06K 9/00885 382/115 |
| 2015/0356285 A1* | 12/2015 | Glaser | G06F 21/32 726/7 |
| 2016/0224773 A1 | 8/2016 | Ramaci | |
| 2018/0101711 A1* | 4/2018 | D'Souza | G06K 9/228 |
| 2019/0087621 A1* | 3/2019 | Khuri-Yakub | G06K 9/00107 |

* cited by examiner

SYSTEMS AND METHODS FOR BIOMETRICALLY AUTHENTICATING A USER USING AUTHENTICATION DATA AND LIVENESS DATA

CROSS-REFERENCE TO RELATED APPLICATION

This application claims the benefit of and priority to U.S. Provisional Patent Application 62/439,706, titled "Financial Transaction System and Access & Activity Granted System with Biometrics, Forensic, Liveness, Fingerprint Technology," filed Dec. 28, 2016, the disclosure of which is incorporated by reference herein.

TECHNICAL FIELD

The present disclosure relates generally to systems and methods for biometrically authenticating a user. In particular, the present disclosure relates to biometrically authenticating a user using biometric data that includes authentication data (e.g., fingerprints, vein pattern, and bone structure) and liveness data (e.g., blood flow).

BACKGROUND

Currently, over 195 million people use mobile payment solutions to purchase goods and services. Conventional mobile payment solutions, however, are susceptible to spoofing and hacking that can result in, for example, illegal purchases and/or identity theft. In some instances, mobile devices implementing such solutions may be stolen, and the stolen devices may be used to purchase goods and services.

SUMMARY

In one embodiment, a biometric authentication system may include a finger scanner for capturing biometric data from a plurality of sections of a finger of a user. The finger may include a distal section, a medial section, and a proximal section. The biometric authentication system may further include one or more processors configured to cause the finger scanner to capture the biometric data from the plurality of sections of the finger of the user. The biometric data may include authentication data and liveness data. The processors may be further configured to access registered authentication data associated with the user, determine whether the captured authentication data matches the registered authentication biometric data, determine, using the captured liveness data, whether the finger is a live finger, and authenticate the user after the captured authentication data is determined to match the registered authentication data and after the finger is determined to be a live finger.

In another embodiment, a method for biometrically authenticating a user may include capturing biometric data from a plurality of sections of a finger of a user. The finger may include a distal section, a medial section, and a proximal section, and the biometric data may include authentication data and liveness data. The method may further include accessing registered authentication data associated with the user, determining whether the captured authentication data matches the registered authentication biometric data, determining, using the captured liveness data, whether the finger is a live finger, and authenticating the user after the captured authentication data is determined to match the registered authentication data and after the finger is determined to be a live finger.

In yet another embodiment, a non-transitory computer-readable storage medium storing instructions, when executed by a computer may cause the computer to perform a method for biometrically authenticating a user. The method may include capturing biometric data from a plurality of sections of a finger of a user. The finger may include a distal section, a medial section, and a proximal section, and the biometric data may include authentication data and liveness data. The method may further include accessing registered authentication data associated with the user, determining whether the captured authentication data matches the registered authentication biometric data, determining, using the captured liveness data, whether the finger is a live finger, and authenticating the user after the captured authentication data is determined to match the registered authentication data and after the finger is determined to be a live finger.

DETAILED DESCRIPTION

The disclosed systems and methods are capable of authenticating a user using biometric data that includes authentication data and liveness data. The authentication data may be used to determine an identity of the user. For example, authentication data indicative of a user's fingerprint, bone structure, and/or vein patterns may be used to uniquely identity the user. The liveness data may be used to determine that the finger in which the biometric data is captured belongs to a living person. For example, liveness data indicative of blood flow within the finger and/or presence of a pulse in the finger may be used to determine that the finger is a live finger. Such a determination may prevent the use of, for example, an artificial finger to bypass the biometric authentication system.

Furthermore, the disclosed systems and methods may capture the biometric data from at least a plurality of sections of a finger. For example, the disclosed system and methods may capture the authentication data (e.g., fingerprint, bone structure, vein patterns) and the liveness data (e.g., presence of blood flow or pulse) from a distal section, a medial section, and a proximal section of a finger. Capturing the biometric data from a plurality of sections of a finger may decrease the probability of false positive results.

Moreover, the authentication data and/or the liveness data may each include a plurality of types of data. For example, the disclosed systems and methods may capture, as the authentication data, data indicative of fingerprint, data indicative of bone structure, and data indicative of vein patterns. Similarly, the disclosed systems and methods may capture, as the liveness data, data indicative of blood flow and data indicative of a pulse in the finger.

Biometric Authentication System

Figure 1:
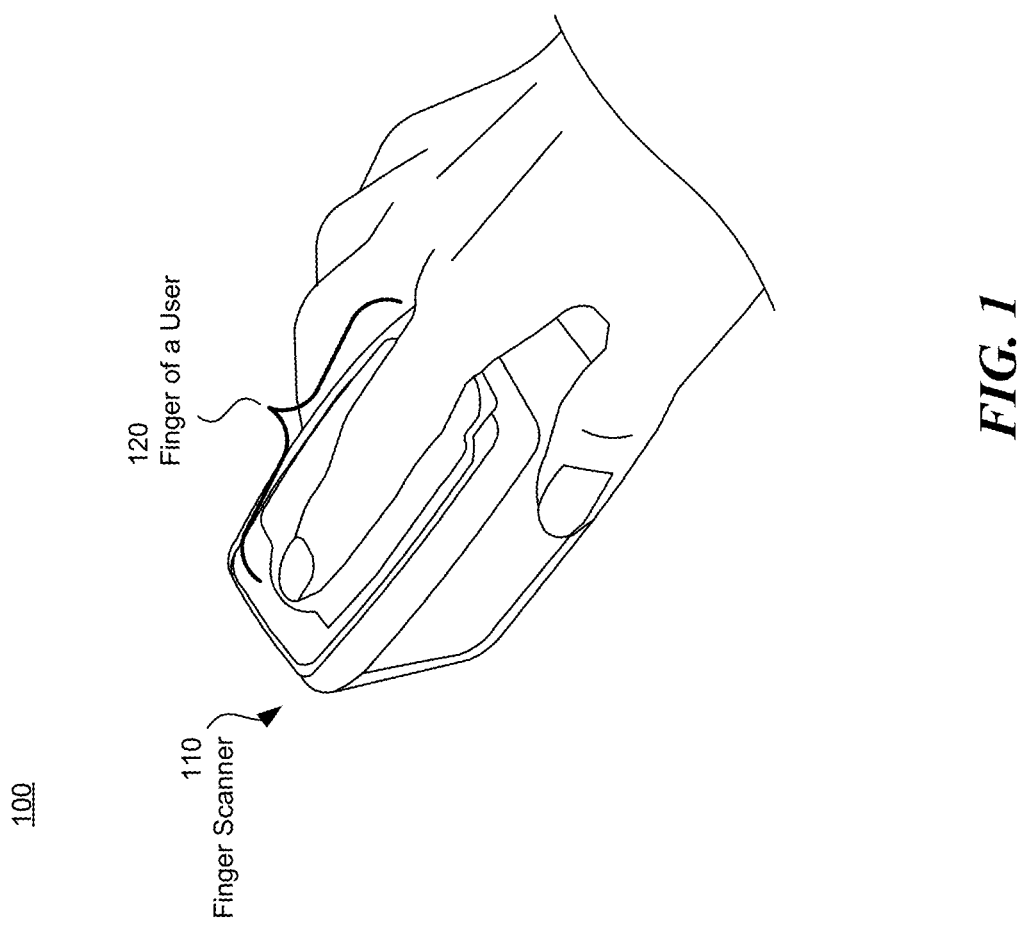
FIG. 1 illustrates an example of a biometric authentication system in accordance with the disclosed embodiments.

FIG. 1 illustrates a biometric authentication system 100 in accordance with the disclosed embodiments. As shown in FIG. 1, system 100 includes a finger scanner 110 for scanning a finger 120 of a user. Finger scanner 110 may be capable of capturing one or more types of biometric data from finger 120 of the user.

In some embodiments, finger scanner 110 may include a platform for supporting finger 120. For example, as shown in FIG. 1, finger scanner 110 may include a glass plate for supporting finger 120 while an image of finger 120 is being captured by a camera below the glass plate. In these embodiments, such a platform may prevent movement of finger 120 while the biometric data is being captured.

In some embodiments, finger scanner 110 may include a set of sensors that can be configured to capture biometric data from any area of finger 120 (e.g., palm side, rear side, left side, and/or right side). In some embodiments, the set of sensors may capture the biometric data from a plurality of areas. In these embodiments, the biometric data from the plurality of area may be captured simultaneously. For example, finger scanner 110 may include a plurality of sensors positioned to capture biometric data from all sides of finger 120. Alternatively, or additionally, a portion of the biometric data may be captured from a first set of areas of finger 120, and subsequently, another portion of the biometric data may be captured from a second set of areas of finger 120. For example, finger scanner 110 may include a sensor that rotates around finger 120 to capture all sides of finger 120. In another example, finger scanner 110 may include a sensor that moves from the distal end to proximal end.

In some embodiments, finger scanner 110 may be capable of capturing data indicative of fingerprints from finger 120. As used herein, a fingerprint may refer to patterns of friction ridges on at least a portion of skin on finger 120.

In some embodiments, finger scanner 110 may be capable of capturing data indicative of bone structure of finger 120. For example, finger scanner 110 may be capable of measuring dimensions of one or more bones inside finger 120. In particular, finger scanner 110 may be capable of measuring length, width, and/or thickness of distal phalanx, medial phalanx, and/or proximal phalanx of finger 120. In another example, finger scanner 110 may be capable of capturing data indicative of shapes (e.g., two- and/or three- dimensional shapes) of one or more bones inside finger 120.

In some embodiments, finger scanner 110 may include an ultrasonic imaging subsystem capable of capturing the data indicative of bone structure of finger 120. The ultrasonic imaging subsystem may scan finger 120 down to a certain level of infiltration under the user's layers of finger skin, veins, muscles, tissue, vessels, nerves, and tendons to reach the user's bone. Once infiltration to the user's bone is achieved, the ultrasonic imaging sensor may capture images of the user's bone.

Alternatively, or additionally, finger scanner 110 may include a low-dose x-ray imaging subsystem capable of capturing bone structure of finger 120.

In some embodiments, finger scanner 110 may be capable of capturing data indicative of vein patterns in finger 120. For example, in some embodiments, finger scanner 110 may emit near-infrared light, which is absorbed by deoxyhemoglobin in human blood, making the vein patterns of finger 120 visible as a series of dark lines. These dark lines may be captured by an image sensor of finger scanner 110. In these embodiments, finger scanner 110 may include a light emitter (e.g., LED) capable of emitting near-infrared light towards finger 120 and an image sensor (e.g., CMOS-based image sensor and/or Charge-couple Device (CCD) image sensor) capable of capturing the dark lines that appear when finger 120 is emitted with the near-infrared light.

In some embodiments, the image sensor may prevent bleeding of vein pattern images into other nearby pixels (i.e., "blooming").

In some embodiments, system 100 may implement minutia-based alignment and Local Binary Pattern (LBP) based extraction process that combines certain minutia points including, but not limited to, bifurcation and ending points of the finger vein region for image alignment, identifying several extracted minutia points and alignment, which can be performed at fast computational speed and the extraction of the user's unique finger vein code using a LBP, which reduces false identifications and errors significantly.

Vein patterns are unique to each individual, even among identical twins. As veins are located inside a finger, it is difficult to steal, spoof, reverse engineer, or fake. Further, finger veins do not leave any trace and are not affected by the weather, physical condition, medical condition, cuts, perspiration, scars, rough or cracked skin, or aging of the user. In some embodiments, biometric authentication using vein patterns may have less than 0.0001% for the False Acceptance Rate (FAR), 0% for the Failure to Enroll (FTE), and less than 0.01% for the False Rejection Rate (FRR).

In some embodiments, finger scanner 110 may be capable of detecting blood flow to finger 120.

In some embodiments, finger scanner 110 may be capable of measuring heart rate of the user via finger 120.

In some embodiments, finger scanner 110 may be capable of measuring an instant pulse on finger 120.

In some embodiments, finger scanner 110 may include one or more processors. In these embodiments, the processors may process the captured biometric data. For example, the processors may apply image filters and/or noise filters to the captured biometric data. In some embodiments, finger scanner 110 may be connected to another computer system that includes one or more processors. In these embodiments, finger scanner 110 may transmit the captured biometric data to the computer system, and the processors of the computer system may process the captured data.

In some embodiments, finger scanner 110 may include one or more storage device. Alternatively, or additionally, finger scanner 110 may include, or connected to, a database.

Figure 2:
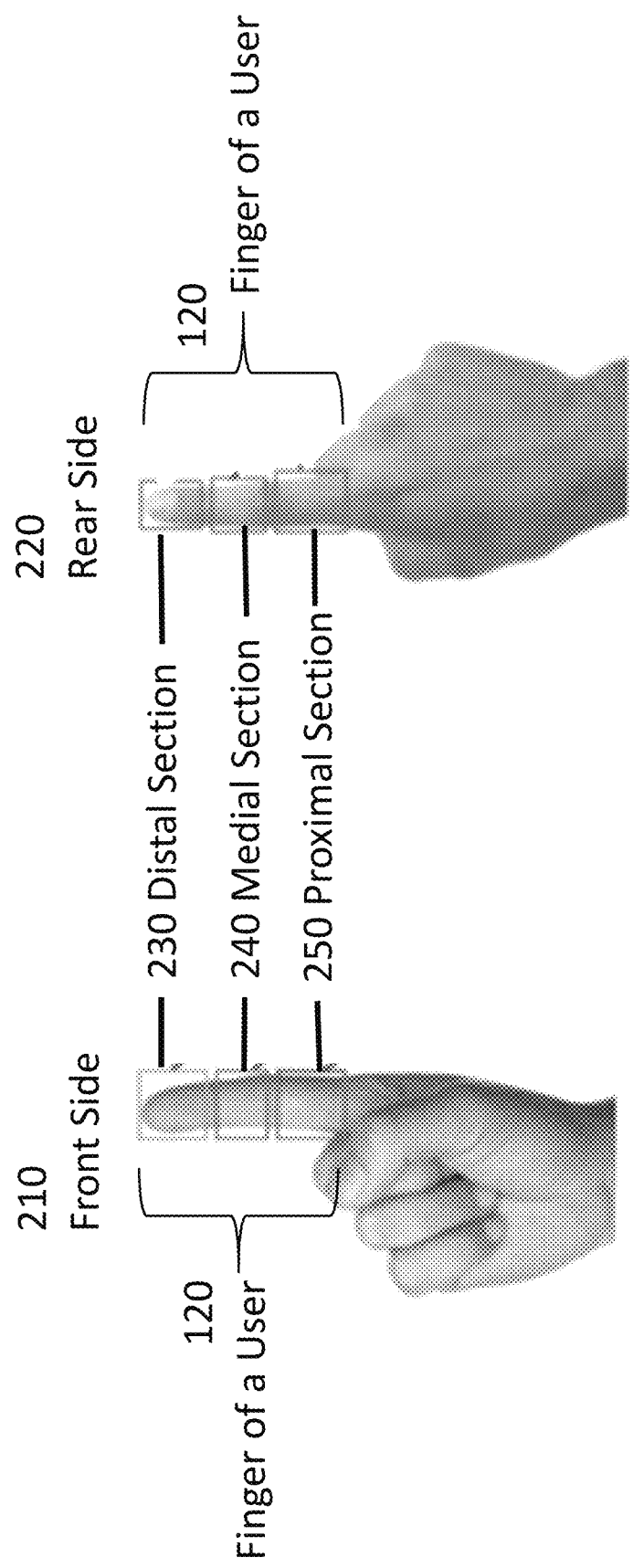
FIG. 2 illustrates various sections of a finger in which biometric data may be captured by a finger scanner in accordance with the disclosed embodiments.

FIG. 2 illustrates various sections of finger 120 in which biometric data may be captured by finger scanner 110 of FIG. 1 in accordance with the disclosed embodiments. As shown in FIG. 2, finger 120 may include a distal section 230, a medial section 240, and a proximal section 250. Further, each section of finger 120 may include a front side 210 and a rear side 220.

In some embodiments, finger scanner 110 may capture biometric data (e.g., fingerprint, vein pattern, bone structure, blood flow, and/or pulse) from one section of finger 120.

Alternatively, finger scanner 110 may capture biometric data from a plurality of sections of finger 120.

In some embodiments, finger scanner 110 may capture biometric data from one side of each section of finger 120 that is scanned by finger scanner 110. For example, finger scanner 110 may capture data indicative of fingerprint from front side 210 of distal section 230 of finger 120. In another example, finger scanner 110 may capture data indicative of fingerprint from front side 210 of medial section 240 and rear side 220 of proximal section 250 of finger 120. In some embodiments, finger scanner 110 may capture biometric data from both sides of each section of finger 120 that is scanned by finger scanner 110. Alternatively, in some embodiments, finger scanner 110 of FIG. 1 may capture biometric data from one side of at least one section of finger 120 and both sides of at least one section of finger 120. For example, finger scanner 110 may capture data indicative of fingerprint from front side 210 of distal section 230 and fingerprint from both front Side 210 and rear side 220 of medial section 240 of finger 120.

In some embodiments, finger scanner 110 may capture a set of biometric data from a section of finger 120 and another set of biometric data from another section of finger 120. For example, finger scanner 110 may capture data indicative of vein patterns and data indicative of bone structure from distal section 230 and medial section 240 of finger 120 and capture data indicate of fingerprint from all three sections of finger 120. In another example, finger scanner 110 may capture data indicative of vein patterns from distal section 230 of finger 120, data indicative of bone structure from medial section 240 of finger 120, and data indicative of fingerprint from proximal section 250 of finger 120.

Figure 3:
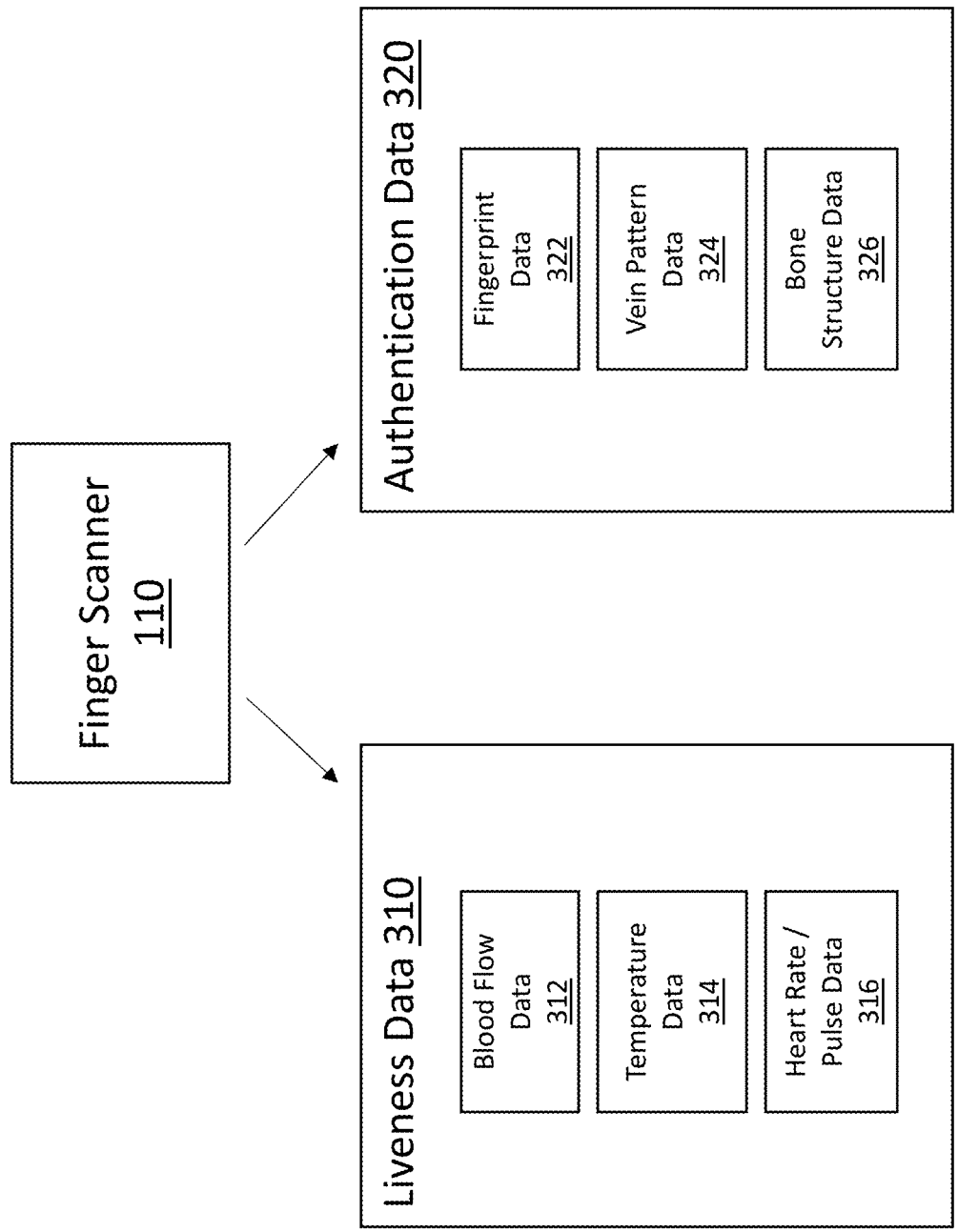
FIG. 3 illustrates an example of biometric data that can be captured by a finger scanner of a biometric authentication system in accordance with the disclosed embodiments.

FIG. 3 illustrates biometric data that can be captured using finger scanner 110. As shown in FIG. 3, the biometric data captured using finger scanner 110 may include liveness data 310 and authentication data 320.

Liveness data 310 may include any biometric data that can be used to determine that finger 120 scanned by finger scanner 110 belongs to a living person. In some embodiments, capturing liveness data 310 may include detecting blood flow 312 within finger 120. For example, presence of blood flow 312 within finger 120 may indicate that finger 120 belongs to a living person. In some embodiments, capturing liveness data 310 may include measuring temperature 314 of finger 120. For example, a normal body temperature measured on finger 120 may indicate that finger 120 belongs to a living person. In some embodiments, capturing liveness data 310 may include detecting instant pulse on finger 120. For example, existence of pulse 316 on finger 120 may indicate that finger 120 belongs to a living person. In some embodiments, capturing liveness data 310 may include detecting a heart rate 316 via finger 120. For example, a detected heart rate 316 that is in range of a normal human heart rate (e.g., 50 bpm to 200 bpm) may indicate that finger 120 belongs to a living person.

Authentication data 320 may include any biometric data that may be unique to the user and substantially immutable over time. In some embodiments, authentication data 320 may include data indicative of fingerprint 322 (e.g., captured from one or more sections of finger 120). In some embodiments, authentication data 320 may include data indicative of vein patterns 324 of finger 120. In some embodiments, authentication data 326 may include data indicative of bone structure 326 of finger 120. For example, finger scanner 110 may capture width, thickness, and/or length of one or more bones (e.g., distal phalanx, medial phalanx, and/or proximal phalanx) in finger 120.

In some embodiments, authentication data 326 may include data indicative of a DNA sequence. In some embodiments, authentication data 326 may include data indicative of blood type.

In some embodiments, a type of biometric data may be both liveness data 310 and authentication data 320.

Examples of Processes

Figure 4:
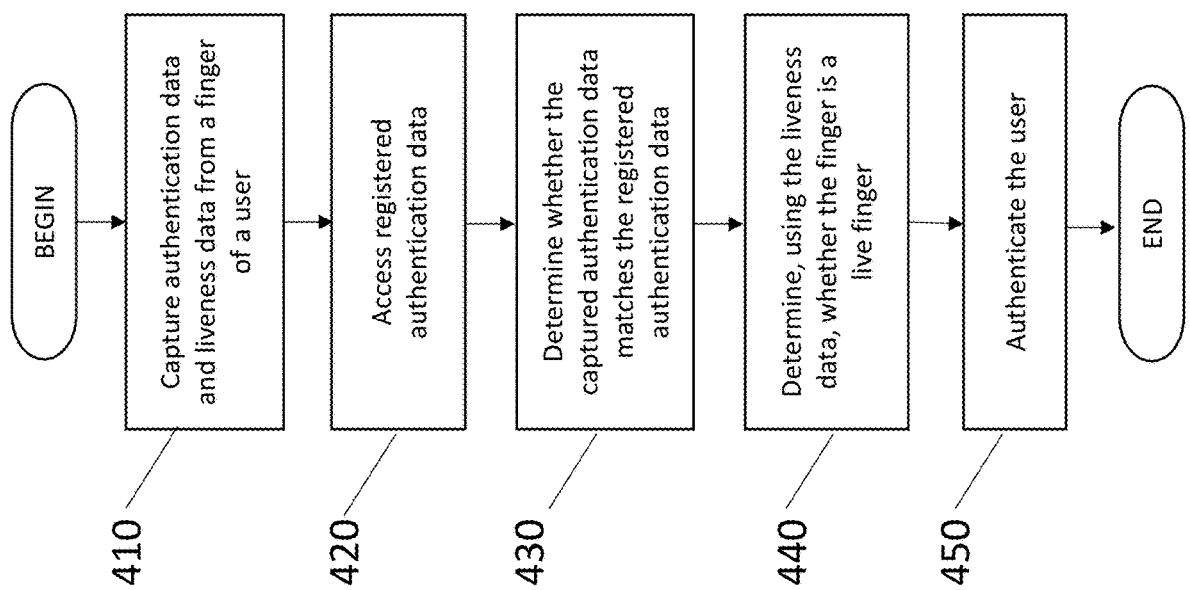
FIG. 4 illustrates an example of a process for biometrically authenticating a user in accordance with the disclosed embodiments.

FIG. 4 illustrates a process 400 for biometrically authenticating a user in accordance with the disclosed embodiments.

At a step 410, finger scanner 110 may capture biometric data that includes authentication data 320 and liveness data 310 from a finger 120 of a user.

As discussed with respect to FIG. 3, the captured authentication data 320 may include any biometric data that may be unique to the user and substantially immutable over time. Liveness data 310 may include any biometric data that can be used to determine that finger 120 scanned by finger scanner 110 belongs to a living person.

In an optional step, a processor may process the captured authentication data 320 and/or liveness data 310. For example, the captured data may be processed using one or more filters to enhance contrast and/or remove noise.

At a step 420, a processor may access registered authentication data for the user. The registered authentication data may be authentication data that was previously captured for the user, for example, during a registration process. In some embodiments, accessing the registered authentication data may include accessing a database that contains authentication data registered to a plurality of users. In some embodiments, a processor may access the registered authentication data from a storage device included in, and/or connected to, finger scanner 110 or a computer system that includes the processor.

In some embodiments, accessing the registered authentication data for the user may include identifying one or more user accounts associated with the authentication data. Since different fingers of a user are associated with different authentication data, a user may assign different user accounts to his or her fingers. For example, the index finger on the user's right hand may be associated with a user account for a social network while the middle fingers on the left hand and the right hand are associated with a user account for a computer network. In another example, the thumb on the right hand may be associated with a checking account at a bank while a pinky finger on the left hand is associated with a savings account at the same bank.

Additionally, or alternatively accessing the registered authentication data for the user may include identifying one or more payment methods associated with the authentication data. For example, the index fingers of the left and right hands may be associated with a credit card while the pinky fingers of the left and right hands are associated with a debit card.

At a step 430, a processor may determine whether the captured authentication data matches the registered authentication data in some embodiments, a processor may determine whether the captured authentication data matches the registered authentication data by comparing the captured authentication data with the registered authentication data. In some embodiment, the processor may determine that the captured authentication data matches the registered authentication data if at least a predetermined portion of the captured authentication data matches the registered authentication data.

At a step 440, a processor may determine, using the liveness data, whether the finger is a live finger. In some embodiments, the liveness data may be used to determine whether the finger is an artificial finger, such as a peeled skin, electronic pulse machines, heart rate machines, computer software generated liveness duplications, skin from animals.

In some embodiments, a processor may attempt to identify abnormalities and unnaturalness of the captured liveness data. For example, a processor may identify unnatural changing patterns of distinct separated areas, including, but not limited to distorted boundary shapes, abnormal peaks found in a histogram distribution, discoloration, appearance inconsistencies such as partially dark areas, pore distribution, large movements of core parts, and ridge sharpness. In some embodiments, a processor may determine if finger 120 is made from materials such silicone, rubber, film, stamp, paper, glue, carbon, paint, Play-Doh, clay, gelatin, food, residue, glass, plastic, carbons, etc.

At a step 450, the processor may authenticate the user after determining that the captured authentication data matches the registered authentication data and after determining that the finger is a live finger.

In an optional step, after authenticating the user, the processor may transmit an indication to another system or a subsystem that the user has been authenticated. The indication may include, for example, an identifier associated with the user. For example, after authenticating the user, the processor may transmit an indication to a software program executing on another computer system that the user has been authenticated along with a username associated with the user. Additionally, or alternatively, in embodiments where one or more user accounts and/or payment methods are associated with the authentication data (e.g., at step 420), the processor may transmit information associated with the user account(s) and/or payment method(s) to another system or a subsystem. For example, the processor may transmit an identifier associated with the user account. In another example, the processor may transmit credit card details of a credit card associated with the authentication data.

In another optional step, after authenticating the user, the processor may cause processing of a transaction. For example, after authenticating the user, the processor may cause a financial transaction to be processed. In embodiments where one or more user accounts and/or payment methods are associated with the authentication data (e.g., at step 420), the processor may cause processing of the transaction using the user account(s) and/or payment method(s). For example, in situations where the authentication data is associated with a payment method, a financial transaction may be processed using the payment method. In another example where the authentication data is associated with a user account of a social network, the processor may cause the user to be logged into the social network using the user account.

In yet another optional step, after authenticating the user, the processor may cause output of an indication that the user has been authenticated. For example, after authenticating the user, the processor may cause output of a text (e.g., "John Doe is Successfully Authenticated) on a display connected to the biometric authentication system. In embodiments where one or more user accounts and/or payment methods are associated with the authentication data (e.g., identified at step 420), the processor may cause output of information associated with the user account(s) and/or payment method(s). For example, the processor may output membership status (e.g., loyalty status) associated with the associated user account. In another example, the processor may cause output of credit card details (e.g., card number, expiration date) of the credit card associated with the authentication data.

Examples of Applications

Figure 5:
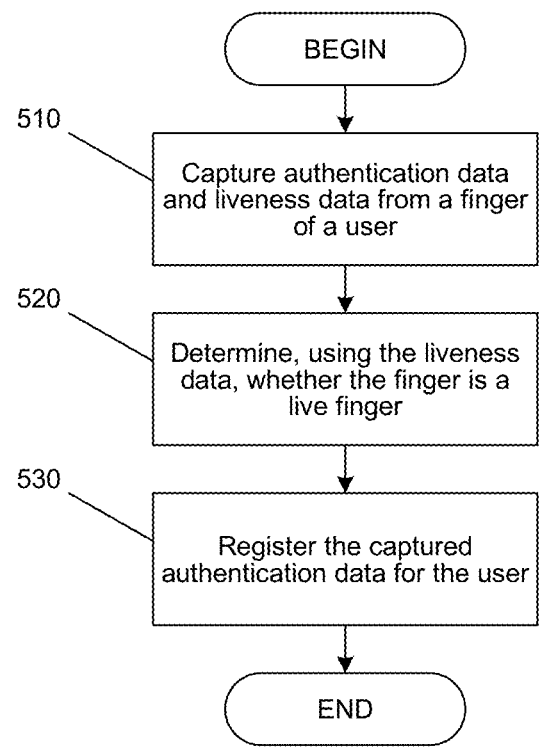
FIG. 5 illustrates an example of a process for registering biometric authentication data for a user in accordance with the disclosed embodiments.

FIG. 5 illustrates an example of a process 500 for registering biometric authentication data for a user in accordance with the disclosed embodiments. In some embodiments, process 500 may be implemented in one or more devices located in banks, Post Offices, DMVs, and shopping malls.

At a step 510, finger scanner 110 may capture biometric data that includes authentication data and liveness data from finger 120 or a user. In some embodiments, finger scanner 110 may capture authentication data and/or liveness data from a plurality of fingers of the user.

At a 520, a processor may determine, using the liveness data, whether finger 120 is a live finger.

At a step 530, after determining that finger 120 is a live finger, a processor may register the captured authentication data for the user. In some embodiments, a processor may receive personal information associated with the user. In some embodiments, the registration of the captured authentication data may include storing the captured authentication data and associating the data with the user. The captured authentication data may be stored, for example, in a storage device included in finger scanner 110 or a storage device of a computer system connected to finger scanner 110. In some embodiments, registering of finger 120 may include associating finger 120 with one or more user accounts and/or payment methods.

Figure 6:
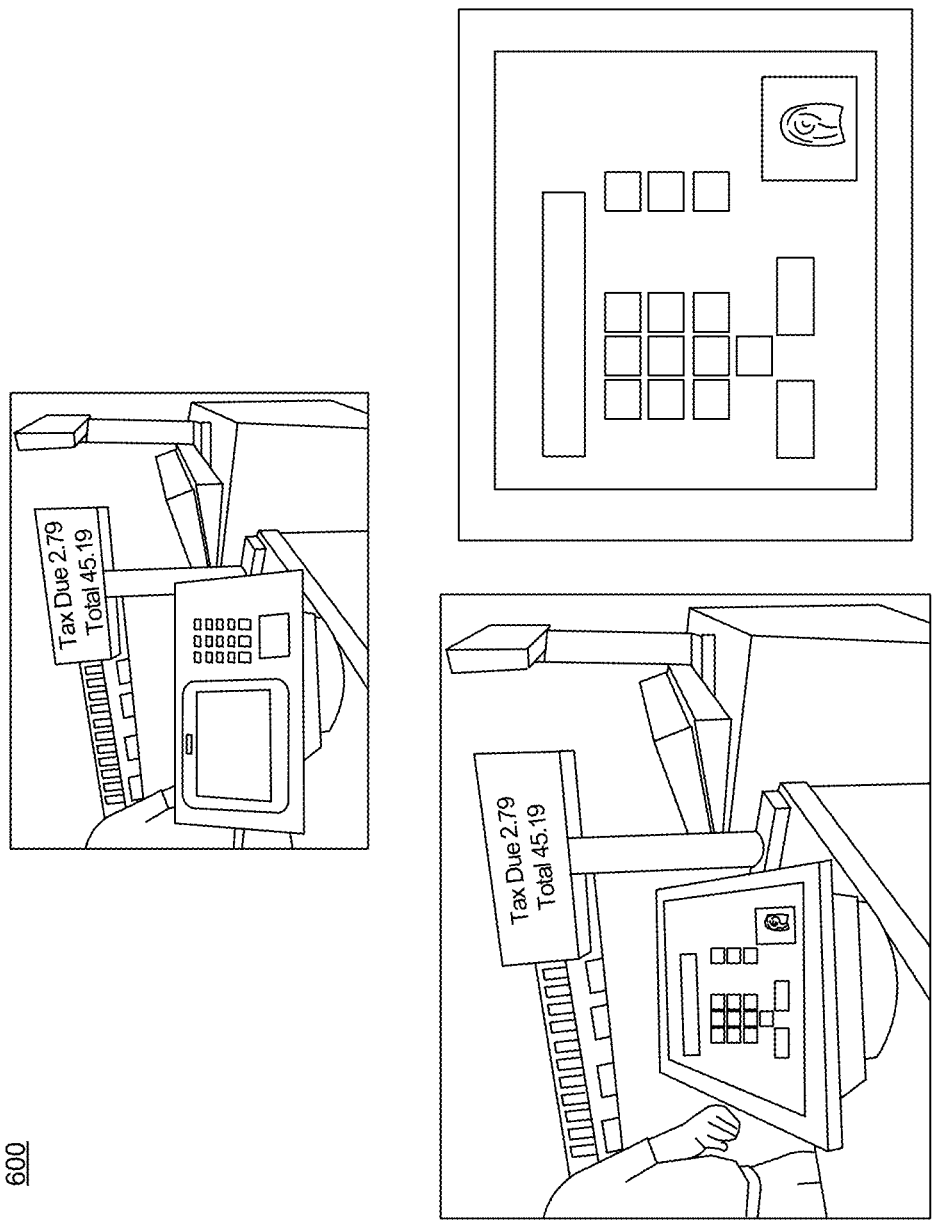
FIG. 6 illustrates an example of a biometric authentication system implemented on a point-of-sale (POS) terminal in accordance with the disclosed embodiments.

FIG. 6 illustrates an example of a biometric authentication system implemented on a point-of-sale (POS) terminal in accordance with the disclosed embodiments. In the system of FIG. 6, biometric authentication system 100 may be integrated in a POS terminal used in various retail stores.

In the system of FIG. 6, after a user places one of his or her fingers on the finger scanner 110, the system may capture biometric data from the finger and authenticate the user. Subsequently, after the authentication, the system may process a payment. The payment may be processed using a payment method (e.g., a credit card or a cryptocurrency wallet) associated with the user or the authentication data. In some embodiments, once the finger is released from finger scanner 110, the system may prevent any additional payments from being processed. That is, if the original user wants to make any additional payments, the user will need to place his or her finger (the same or different) on finger scanner 110 again.

Figure 7:
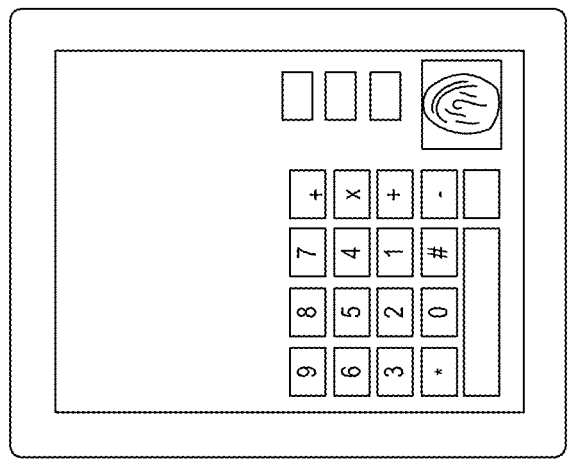
FIG. 7 illustrates an example of a biometric authentication system implemented on a pay-at-the-table device in accordance with the disclosed embodiments.
Figure 7:
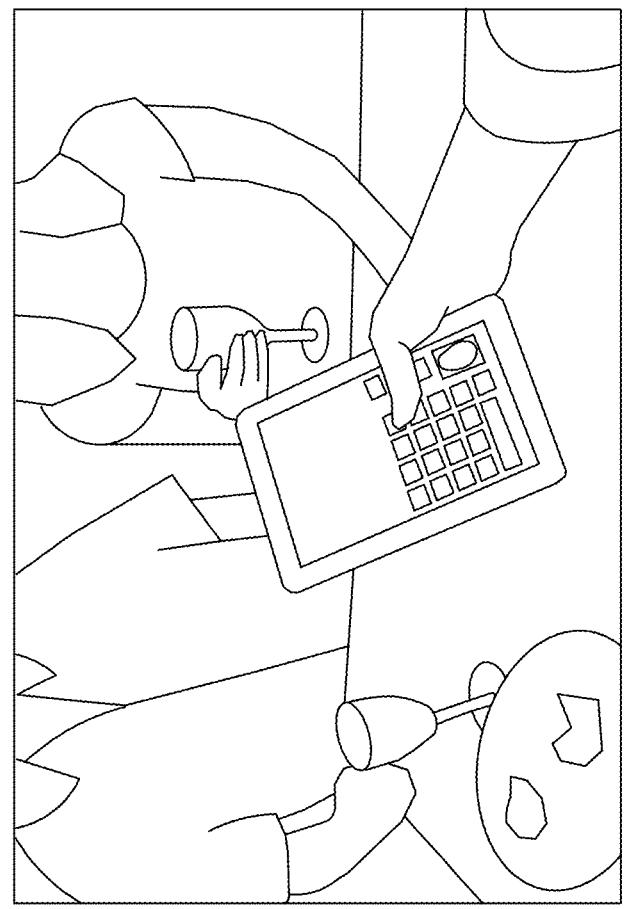

FIG. 7 illustrates an example of a biometric authentication system implemented on a pay-at-the-table device in accordance with the disclosed embodiments. The system of FIG. 7 may be used in restaurants and retailers to enable customers to make secure and quick payments using a portable device anywhere within the business premise. Such a system may be operated by an employee of the businesses, who can ensure that the finger scanned by finger scanner 120 is indeed the real finger of the customer.

Figure 8:
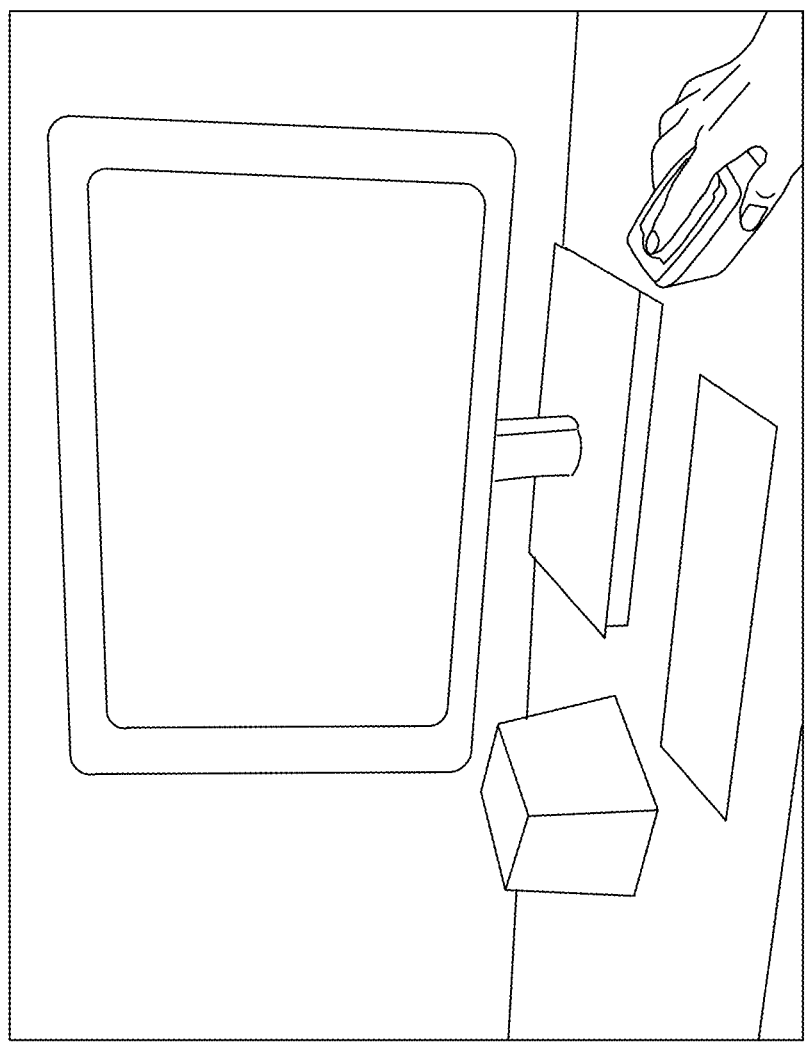
FIG. 8 illustrates an example of a biometric authentication system that can be connected to a computer in accordance with the disclosed embodiments.

FIG. 8 illustrates an example of a biometric authentication system that can be connected to a computer in accordance with the disclosed embodiments. The biometric authentication system of FIG. 8 may interface with other systems, such as another computer system. In the example of FIG. 8, the biometric authentication system may be used to authenticate a user for various software programs executing on the computer system. For example, the biometric authentication system may be used to authenticate a user for an operating system executing on the computer system or to authenticate a user for a website accessed using the computer system.

Figure 9:
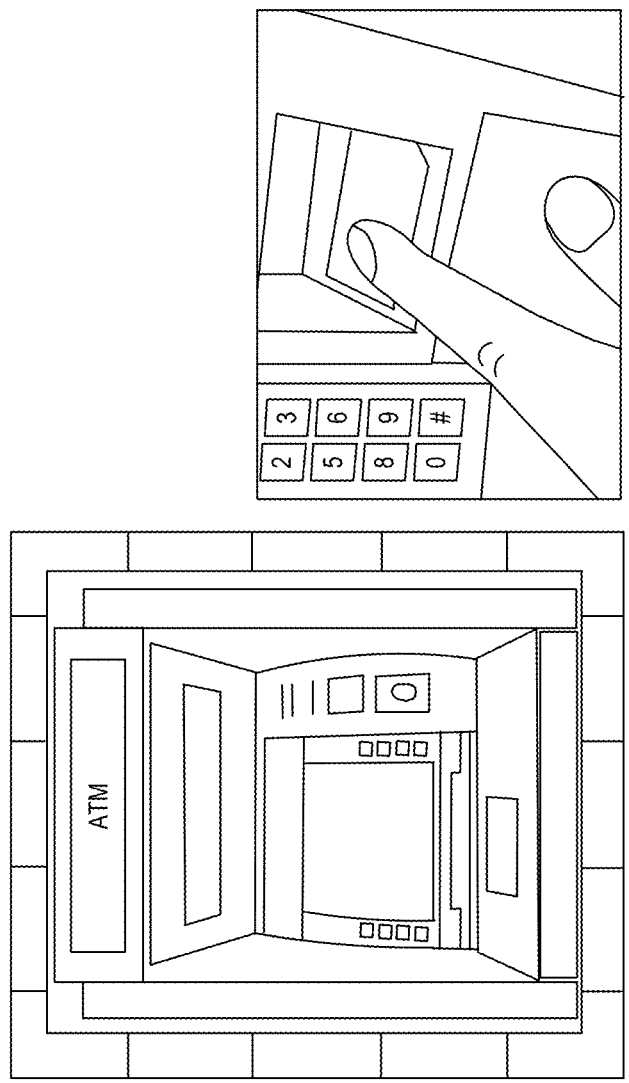
FIG. 9 illustrates an example of a biometric authentication system that can be implemented on an automatic teller machine (ATM) in accordance with the disclosed embodiments.

FIG. 9 illustrates an example of a biometric authentication system that can be implemented on an automatic teller machine (ATM) in accordance with the disclosed embodiments. In the example of FIG. 9, instead of a passcode, biometric authentication system 100 may be used to authenticate a user.

Moreover, in some embodiments, the disclosed biometric authentication systems and methods may be implemented in devices used for retail purchases and devices for accepting credit and debit payments, such as stores, venues, clubs, events, online purchases, outlets, businesses. In some embodiments, the disclosed biometric authentication systems and methods may be used for fool-proof identification, including but not limited to medical registration, hospital entry or loitering identification, doctor/nurse/medical staff identification and authorization, hospital/patient room entry, patient identification, surgeon and medical assistant identification, new born baby identification in hospitals, multiple baby identification (twins, triplets, etc.), prescriptions/drugs identification, voter registration, lawful entry, hotel entry, property entry, criminal identification, school personnel identification, police identification, military identification, business and home service identification (plumber, gas, water, electric, home improvement, landscape, etc.), jail/prison, personal records, electronic musical instrument power or select features authorization, electronic device activation (computer, phones, radios, etc.), office equipment entry (desk, file cabinets, etc.), classified high-security entry, transportation identification and authorization, for start/shut off of vehicles, carnival and circus employees identification (e.g., when costumes are on), weaponry such as guns, rifles, assault, firearms, etc.

From the foregoing, it will be appreciated that specific embodiments of the invention have been described herein for purposes of illustration, but that various modifications may be made without deviating from the scope of the invention. Accordingly, the invention is not limited except as by the appended claims.

I claim:

1. A biometric authentication system, comprising:
    a finger scanner for capturing biometric data from a plurality of sections of a finger of a user, the finger including a distal section, a medial section, and a proximal section at a same time; and
    one or more processors configured to:
        cause the finger scanner to simultaneously capture the biometric data from each of the plurality of sections of the finger of the user, wherein the biometric data includes both authentication data and liveness data, where the liveness data includes data indicative of each of a blood flow in the finger, a temperature of the finger and one of a heart rate or a pulse in the finger;
        access registered authentication data associated with the user;
        determine whether the captured authentication data from each of the plurality of finger sections matches the registered authentication biometric data;
        determine, using the captured liveness data, whether the finger is a live finger; and
        authenticate the user after the captured authentication data is determined to match the registered authentication data and after the finger is determined to be a live finger.

2. The system of claim 1, wherein the authentication data includes front-side fingerprints from the plurality of sections of the finger.

3. The system of claim 1, wherein the biometric authentication system is included in one of: automatic teller machine (ATM), point-of-service (POS) terminal, and a portable electronic device.

4. The system of claim 1, wherein the authentication data includes at least one of: vein pattern of the finger and bone structure of the finger.

5. The system of claim 1, wherein the liveness data further includes data indicative of at least one of: boundary shapes, discoloration, pore distribution, and ridge sharpness of the finger.

6. A method for biometrically authenticating a user, the method comprising:
    simultaneously capturing biometric data from a plurality of sections of a finger of a user, the finger including a distal section, a medial section, and a proximal section, and the biometric data including authentication data and liveness data, where the liveness data includes data indicative of each of a blood flow in the finger, a temperature of the finger and one of a heart rate or a pulse in the finger;
    accessing registered authentication data associated with the user;
    determining whether the captured authentication data matches the registered authentication biometric data;
    determining, using the captured liveness data, whether the finger is a live finger; and
    authenticating the user after the captured authentication data is determined to match the registered authentication data and after the finger is determined to be a live finger.

7. The method of claim 6, wherein the authentication data includes front-side fingerprints from the plurality of sections of the finger.

8. The method of claim 6, wherein the method is performed by one of: automatic teller machine (ATM), point-of-service (POS) terminal, and a portable electronic device.

9. The method of claim 6, wherein the authentication data includes at least one of: vein pattern of the finger and bone structure of the finger.

10. The method of claim 6, wherein the liveness data further includes data indicative of at least one of: boundary shapes, discoloration, pore distribution, and ridge sharpness of the finger.

11. A non-transitory computer-readable storage medium storing instructions that when executed by a computer cause the computer to perform a method for biometrically authenticating a user, the method comprising:
    simultaneously capturing biometric data from a plurality of sections of a finger of a user, the finger including a distal section, a medial section, and a proximal section, and the biometric data including authentication data and liveness data, where the liveness data includes data indicative of each of a blood flow in the finger, a temperature of the finger and a heart rate or a pulse in the finger;
    accessing registered authentication data associated with the user;
    determining whether the captured authentication data matches the registered authentication biometric data;
    determining, using the captured liveness data, whether the finger is a live finger; and
    authenticating the user after the captured authentication data is determined to match the registered authentication data and after the finger is determined to be a live finger.

12. The non-transitory computer-readable storage medium of claim 11, wherein the authentication data includes front-side fingerprints from the plurality of sections of the finger.

13. The non-transitory computer-readable storage medium of claim 11, wherein the computer is one of: automatic teller machine (ATM), point-of-service (POS) terminal, and a portable electronic device.

14. The non-transitory computer-readable storage medium of claim 11, wherein the authentication data includes at least one of: vein pattern of the finger and bone structure of the finger.

15. The non-transitory computer-readable storage medium of claim 11, wherein the liveness data further includes data indicative of at least one of: boundary shapes, discoloration, pore distribution, and ridge sharpness of the finger.

* * * * *